United States Patent [19]

Martin et al.

[11] Patent Number: 4,648,895
[45] Date of Patent: * Mar. 10, 1987

[54] OXIME ETHERS, THE PREPARATION THEREOF, COMPOSITIONS CONTAINING THEM AND USE THEREOF

[75] Inventors: Henry Martin, Allschwil; Urs Fricker, Gelterkinden, both of Switzerland

[73] Assignee: Ciba-Geigy Corporation, Ardsley, N.Y.

[*] Notice: The portion of the term of this patent subsequent to Sep. 23, 2002 has been disclaimed.

[21] Appl. No.: 699,488

[22] Filed: Feb. 8, 1985

Related U.S. Application Data

[63] Continuation of Ser. No. 481,683, Apr. 4, 1983, abandoned.

[30] Foreign Application Priority Data

Apr. 16, 1982 [CH] Switzerland ............... 2326/82

[51] Int. Cl.$^4$ .................. A01N 43/00; C07D 317/00
[52] U.S. Cl. ......................................... 71/88; 549/451
[58] Field of Search ........................... 549/451; 71/88

[56] References Cited

U.S. PATENT DOCUMENTS

| | | | |
|---|---|---|---|
| 4,269,775 | 5/1981 | Szczepanski et al. | 544/163 |
| 4,468,242 | 8/1984 | Szczepanski et al. | 71/88 |
| 4,497,648 | 2/1985 | Szczepanski et al. | 71/88 |
| 4,530,716 | 7/1985 | Martin et al. | 71/88 |

FOREIGN PATENT DOCUMENTS 0089313  9/1983  European Pat. Off. ............ 549/451

*Primary Examiner*—Ethel G. Love
*Attorney, Agent, or Firm*—Edward McC. Roberts; Bruce M. Collins

[57] ABSTRACT

The invention relates to oxime ethers of the formula I

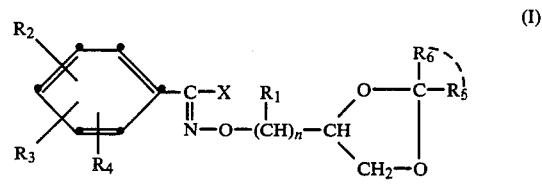

(I)

wherein n is 1 or 2, each of $R_1$ and $R_2$ is hydrogen or $C_1$–$C_4$ alkyl each of $R_3$ and $R_4$ is hydrogen, halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ haloalkylthio, $C_1$–$C_4$ alkylsulfinyl, $C_1$–$C_4$ alkylsulfonyl, $C_1$–$C_4$ haloalkylsulfinyl, $C_1$–$C_4$ haloalkylsulfonyl or nitro; each of $R_5$ and $R_6$ independently of the other is hydrogen, $C_1$–$C_4$ alkyl, $C_1$–$C_4$ haloalkyl, phenyl or phenyl which is substituted by halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, carboxyl, carbamoyl, $C_1$–$C_4$ alkylcarbamoyl, nitro or cyano, or $R_5$ and $R_6$ together are also a 2- to 6-membered alkylene or alkenylene chain which may be substituted by $C_1$–$C_4$ alkyl radicals; X is hydrogen, cyano, nitro, chlorine, $C_1$–$C_4$ alkyl, $C_1$–$C_4$ haloalkyl, $C_3$–$C_6$ cycloalkyl, carboxyl, carbamoyl, $C_1$–$C_4$ alkylcarbonyl, $C_1$–$C_4$ alkoxycarbonyl or $C_1$–$C_4$ alkylcarbamoyl.

The oxime ethers of the formula I are able to act as antidotes or safeners to protect cultivated plants from the phytotoxic effects of herbicides. Such cultivated plants are preferably sorghum, cereals, maize and rice.

13 Claims, No Drawings

OXIME ETHERS, THE PREPARATION THEREOF, COMPOSITIONS CONTAINING THEM AND USE THEREOF

CROSS REFERENCE

This is a continuation of Ser. No. 481,683, filed Apr. 4, 1983, now abandoned.

The present invention relates to novel oxime ethers, to the preparation thereof, to compositions for protecting cultivated plants from the phytotoxic effects of herbicides, which compositions contain the novel oxime ethers as active component, and to the use thereof.

It is known that herbicides belonging to a very wide range of compound classes such as triazines, urea derivatives, carbamates, thiocarbamates, haloacetanilides, halophenoxyacetic acids etc., when employed in an effective concentration, sometimes also damage cultivated plants to a certain extent in addition to the weeds which it is desired to control. To counteract this problem, different compounds have already been proposed which are able specifically to antagonise the harmful action of the herbicide on the cultivated plant, i.e. to protect the cultivated plant without noticeably influencing the herbicidal action on the weeds to be controlled. However, it has been found that the proposed antidotes very often have a species-specific activity both with respect to the cultivated plants and to the herbicide and also, in some cases, contingent on the mode of application, i.e. a specific antidote is often suitable only for a specific cultivated plant and a few classes of herbicides.

For example, British patent specification 1 277 567 describes the protective treatment of seeds or seedlings of wheat and sorghum with certain oxamic acid esters and amides against attack by "ALACHLOR" (N-methyoxymethyl-N-chloroacetyl-2,6-diethylaniline). Antidotes for treating cereals, maize and rice seeds against the harmful effects of herbicidal thiocarbamates are proposed in German Offenlegungsschrift specifications 1 952 910 and 2 245 471 and in French patent specification 2 021 611. German patent specification 1 576 676 and U.S. Pat. No. 3,131,509 disclose the use of hydroxyaminoacetanilides and hydantoins for protecting cereal seeds against the effects of carbamates.

The direct pre- or postemergence treatment of certain useful plants with antidotes as antagonists of specific classes of herbicides in a crop area is disclosed in German Offenlegungsschrift specifications 2 141 586 and 2 218 097 and in U.S. Pat. No. 3,867,444.

Further, German Offenlegungsschrift 2 402 983 discloses that maize plants can be effectively protected against damage by chloroacetanilides by adding an N-disubstituted dichloroacetamide as antidote to the soil.

According to European patent application 11.047, alkoximinobenzylcyanides, in which the alkoxy group is substituted, inter alia, by an acetalised carbonyl group, can also be used as antidotes for protecting cultivated plants from the harmful effects of herbicides belonging to different classes of compounds.

The present invention relates to novel oxime ethers of the formula I

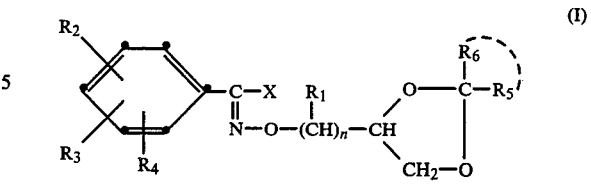

wherein n is 1 or 2, each of $R_1$ and $R_2$ is hydrogen or $C_1$–$C_4$ alkyl each of $R_3$ and $R_4$ is hydrogen, halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ haloalkylthio, $C_1$–$C_4$ alkylsulfinyl, $C_1$–$C_4$ alkylsulfonyl, $C_1$–$C_4$ haloalkylsulfinyl, $C_1$–$C_4$ haloalkylsulfonyl or nitro; each of $R_5$ and $R_6$ independently of the other is hydrogen, $C_1$–$C_4$ alkyl, $C_1$–$C_4$ haloalkyl, phenyl or phenyl which is substituted by halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, $C_1$–$C_4$ alkylsulfinyl, $C_1$–$C_4$ alkylsulfonyl, carboxyl, carbamonyl, $C_1$–$C_4$ alkylcarbamoyl, nitro or cyano, or $R_5$ and $R_6$ together are also a 2- to 6-membered alkylene or alkenylene chain which may be substituted by $C_1$–$C_4$ alkyl radicals; X is hydrogen, cyano, nitro, chlorine, $C_1$–$C_4$ alkyl, $C_1$–$C_4$ haloalkyl, $C_3$–$C_6$ cycloalkyl, carboxyl, carbamoyl, $C_1$–$C_4$ alkylcarbonyl, $C_1$–$C_4$ alkoxycarbonyl or $C_1$–$C_4$ alkylcarbamoyl.

The $C_1$–$C_4$ alkyl groups represented by or contained in the radicals $R_1$ to $R_6$ may be straight chain or branched and are individually methyl, ethyl, n-propyl, isopropyl, n-butyl, sec-butyl, isobutyl and tert-butyl. Among these alkyl groups, $C_1$–$C_2$ alkyl groups are preferred and $R_1$ as alkyl is preferably methyl.

Halogen denotes fluorine, chlorine, bromine and iodine, with fluorine and chlorine being preferred.

The haloalkyl radical X may be e.g. difluoromethyl, trifluoromethyl, chlorodifluoromethyl, tetrafluoroethyl, pentafluoroethyl and heptafluoropropyl. Particularly preferred radicals X are trifluoromethyl and cyano.

The compounds of the formula I, wherein n is 1 and $R_1$ is hydrogen or methyl, $R_2$ is hydrogen, $R_4$ is hydrogen or halogen, and $R_3$, $R_5$, $R_6$ and X are as defined for formula I, are preferred. They correspond to the formula Ia

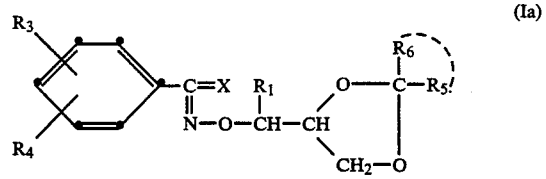

Among these compounds, particularly active compounds are those of the formula Ib or Ic

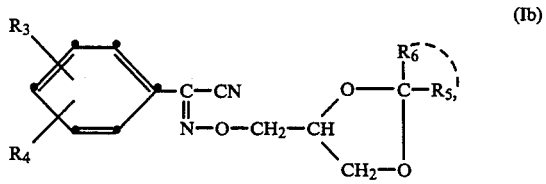

-continued

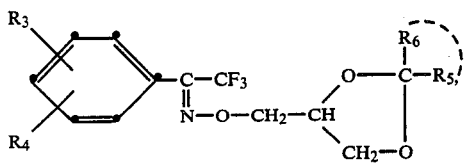
(Ic)

wherein R₃, R₅ and R₆ are as defined for formula I and R₄ is hydrogen or halogen.

Preferred individual compounds are:
N-(1,3-dioxolan-5-yl-methoxy)imino-para-chloro-phenylacetonitrile,
N-(4-methyl-1,3-dioxolan-5-yl-methoxy)imino-para-chclorphenyl-acetonitrile,
1-phenyl-(1,3-dioxolan-5-yl-methoxy)imino-2,2,2-trifluoroethane,
1-(4-chlorophenyl-1,3-dioxolan-5-yl-methoxy)imino-2,2,2-trifluoroethane,
N-(2,2-dimethyl-1,3-dioxolan-5-yl-methoxy)imino-para-chlorophenyl-acetonitrile
N-(1,3-dioxolan-5-yl-methoxy)imino-phenylacetonitrile,
N-(2-methyl-1,3-dioxolan-5-yl-methoxy)imino-ortho-fluorophenyl-acetonitrile,
N-(2-methyl-1,3-dioxolan-5-yl-methoxy)imino-para-tolyl-acetonitrile,
N-(2,2-dimethyl-1,3-dioxolan-5-yl-methoxy)imino-para-tolyl-acetonitrile,
N-(1,3-dioxolan-5-yl-methoxy)imino-para-tolyl-acetonitrile.

The novel oxime ethers of the formula I are prepared by reacting a salt of an oxime of the formula II

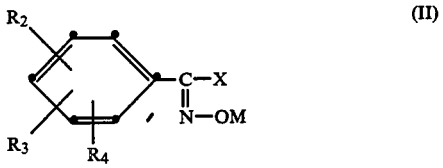
(II)

in which M is an alkali metal cation or an alkaline earth metal cation and R₂, R₃, R₄ and X have the above meanings, with a 5-(α-haloalkyl or β-haloalkyl)-1,3-dioxolane of the formula III

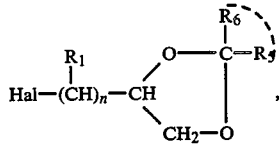
(III)

in which Hal is a halogen atom, preferably a chlorine atom or a bromine atom, and n, R₁, R₅ and R₆ are as defined above. Suitable salts of an oxime of the formula II are in particular the sodium and potassium salts. The reaction of the oxime of formula II with the haloacetal of formula III is conveniently carried out in an inert organic solvent. Particularly suitable solvents are polar solvents such as acetonitrile, dimethylformamide and dimethylsulfoxide.

The reactants are normally employed in equimolar amount. However, an excess of one or other reactant may also be employed to bring the reaction to completion. The reaction is conveniently carried out at elevated temperature, preferably at the reflux temperature of the reaction mixture.

The oximes of formula II, in which X is haloalkyl, may be prepared in known manner by reacting the corresponding ketones with hydroxylamine. The ketones required for the reaction can in turn be obtained by reacting a Grignard compound of the formula IV

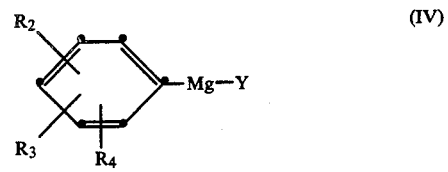
(IV)

wherein Y is chlorine, bromine or iodine, and R₂, R₃ and R₄ are as defined above, with a carboxylic acid X'—COOH, an acid chloride X'—COCl or a nitrile X'—CN, wherein X' is haloalkyl, (cf. U.S. Pat. No. 3,748,361).

The oxime ethers of the formula II, wherein X is cyano, are known compounds (see e.g. U.S. Pat. No. 3,799,757) or they may be prepared by similar methods from benzyl cyanides and alkyl nitrite in the presence of sodium ethylate (Organic Reactions (1953), Vol. 7, pages 343 and 373; European patent specification 6152).

Examples of oximes of the formula II suitable for obtaining the novel oxime ethers of the formula I are:
1-phenyl-1-hydroximino-2,2,2-trifluoroethane
1-(4-methylphenyl)-1-hydroximino-2,2,2-trifluoroethane
1-(4-chlorophenyl)-1-hydroximino-2,2,2-trifluoroethane
1-(4-fluorophenyl)-1-hydroximino-2,2,2-trifluoroethane
1-(4-trifluoromethylphenyl)-1-hydroximino-2,2,2-trifluoroethane
1-(3-trifluoromethylphenyl)-1-hydroximino-2,2,2-trifluoroethane
1-(4-methoxyphenyl)-1-hydroximino-2,2,2-trifluoroethane
1-(4-trifluoromethoxyphenyl)-1-hydroxyimino-2,2,2-trifluoroethane
1-(3-nitrophenyl)-1-hydroximino-2,2,2-trifluoroethane
2-(4-chlorophenyl)-2-hydroximino-acetonitrile
2-(3-chlorophenyl)-2-hydroximino-acetonitrile
2-(2-fluorophenyl)-2-hydroximino-acetonitrile
2-(2,4-dichlorophenyl)-2-hydroximino-acetonitrile
2-(4-fluorophenyl)-2-hydroximino-acetonitrile
2-(4-methylphenyl)-2-hydroxyimino-acetonitrile.
2-(phenyl)-2-hydroyiminoacetonitrile.

The 5-halo-1,3-dioxolanes or 5-(α-haloalkyl)-1,3-dioxolanes of the formula III may be prepared in corresponding manner by reacting halogenated propylene oxide or a 3-haloalkyl-1,2-diol of the formula VI

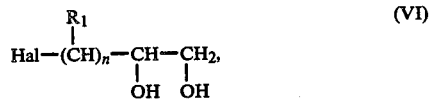
(VI)

wherein Hal is a halogen atom and R₁ is as defined for formula I, with a lower ketone or aldehyde of the formula VII

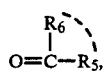

(VII)

wherein $R_5$ and $R_6$ are as defined for formula I.

Examples of suitable 5-halo-1,3-dioxolanes and 5-(α-haloalkyl)-1,3-dioxolanes are:
1-(1,3-dioxolan-5-yl)-1-chloroethane
5-chloromethyl-1,3-dioxolane
5-bromoethyl-1,3-dioxolane
5-chloromethyl-2,2-dimethyl-1,3-dioxolane
5-chloromethyl-2-ethyl-1,3-dioxolane
5-bromomethyl-2-methyl-1,3-dioxolane
5-bromomethyl-2-isopropyl-1,3-dioxolane
5-chloromethyl-2-isobutyl-1,3-dioxolane
5-bromomethyl-2-tert-butyl-1,3-dioxolane
5-bromomethyl-2,2-dimethyl-1,3-dioxolane
5-bromomethyl-2,2-diethyl-1,3-dioxolane
5-(1,3-dioxolan-5-yl)-1-bromoethane
5-(2-methyl-1,3-dioxolan-5-yl)-1-bromoethane
5-(2,2-dimethyl-1,3-dioxolan-5-yl)-1-bromoethane
5-(2-ethyl-1,3-dioxolan-5-yl)-1-bromoethane
5-(5-isopropyl-1,3-dioxolan-5-yl)-1-chloroethane
5-(2-ethyl-2-methyl-1,3-dioxolan-5-yl)-1-chloroethane
5-chloromethyl-2-ethyl-2-methyl-1,3-dioxolane
5-chloromethyl-2,2-cyclopentyliden-1,3-dioxolane
5-chloromethyl-2,2-cyclohexyliden-1,3-dioxolane.

The novel oxime ethers of formula I are most suitble for protecting cultivated plants from damage caused by agrochemicals. This protection extends in particular to herbicides of different compound classes, including 1,3,5-triazines, 1,2,4-triazines, phenylurea derivatives, carbamates, thiocarbamates, phenoxyacetates, phenoxypropionates, haloacetanilides, halophenoxyacetates, substituted phenoxyphenoxyacetates and phenoxyphenoxypropionates, substituted pyridiyloxyphenoxyacetates and pyridyloxyphenoxypropionates, benzoic acid derivatives etc., where these compounds are not tolerated or are insufficiently tolerated by cultivated plants. The novel oxime ethers of formula I are suitable in particular for protecting cultivated plants from the harmful effects of haloacetanilides and thiocarbamates. They can therefore be termed antidotes or also safeners with respect to their use in combination with the herbicides referred to above.

The compounds of the formula I exist in different isomeric forms.

As oxime derivatives, these compounds are obtained in the syn- and anti-form or as mixtures thereof (E- and Z-form, cf. R. S. Cohn et al., Ang. Chemie Int. Ed. 5, (1966), 385, or Experientia 12 (1956), p. 81).

Depending on the substitution of the compounds of formula I, an asymmetrical carbon atom is present and two enantiomers may be obtained. In general, a mixture of both enantiomers is obtained, which mixture can be resolved into the optical antipodes in conventional manner.

The monosubsituted dioxolanes lead to further cis-trans-isomers or mixtures thereof. Disubstituted dioxolanes lead to cis-syn-isomers, cis-anti-isomers and to trans-isomers or mixtures thereof. The number of isomers can be reduced by choice of starting materials, e.g. by using the pure Z-form of the oximes. The present invention also relates to these different isomers and to mixtures thereof.

Depending on the end use, the safener or antidote of the formula I can be used for pretreating seeds of the cultivated plant (dressing of the seeds or seedlings) or it can be added to the soil before or after sowing. However, it can also be applied pre- or post-emergence by itself alone or together with the herbicide. The treatment of the plant or seeds with the antidote can therefore in principle be carried out independently of the time of application of the phytotoxic chemical. It can, however, also be carried out by simultaneous application of phytoxic chemical and antidote (tank mixture). The pre-emergence treatment includes both treatment of the crop area before sowing (ppi=pre-plant incorporation) and treatment of the crop areas after sowing but before emergence of the plants.

The rates of application of the antidote with respect to the herbicide depend largely on the mode of application. Where a field treatment is carried out, either simultaneously as tank mixture or with separate application of herbicide and antidote, the ratio of antidote to herbicide is in the range from 1:100 to 5:1. Full protective action is usually obtained at a ratio of antidote to herbicide of 1:1 to 1:20. When dressing seeds and taking similar specific protective measures, however, much lower amounts of antidote are required compared with e.g. the amounts of herbicide later employed per hectare of crop area. For seed dressing, 0.1 to 10 g of antidote per kg of seeds are required, with the preferred amount being from 1 to 2 grams. If It is desired to apply the antidote shortly before sowing by seed pretreatment, antidote solutions which contain the active ingredient in a concentration of 1 to 10,000 ppm are used. Full protective action is normally obtained with antidote concentrations of 100 to 1000 ppm.

As a rule there is a substantial interval of time between protective meaures such as seed dressing and treatment of seedlings with an antidote of the formula I and the possible later field treatment with agricultural chemicals. Pretreated seeds and plants can later come in contact with different chemicals in agriculture, horticulture and forestry. Accordingly, the invention relates to plant protection compositions which contain an antidote of the formula I as active ingredient, together with conventional carriers. If appropriate, such compositions may be additionally mixed with the chemical against whose effects it is desired to protect the cultivated plant.

Cultivated plants within the scope of this invention are all plants which, in any form, can be harvested (seeds, roots, stalks, tubers, leaves, blossoms) and from which extracts can be obtained (oils, sugar, starch, protein) and which are cultivated for this purpose.

These plants comprise e.g. all species of cereals such as wheat, rye, barley, oats and, in particular, rice, sorghum, maize, and also cotton, sugar beet, sugar can, soybeans, beans, and peas.

The antidote can be employed wherever it is desired to protect a cultivated plant of the kind indicated above from the harmful effects of an agricultural chemical. As already mentioned, possible agricultural chemicals are primarily herbicides of the most widely varying compound classes, in particular haloacetanilides and thiocarbamates.

Numerous haloacetanilides whose harmful effects on cultivated plants can be antagonised with the novel oxime ethers of the formula I are known in the art (q.v. German patent applications 2 305 495, 2 328 340, 2 212 268, 2 726 252 and 2 805 757, and U.S. Pat. Nos.

3,946,044, 4,022,608 and 4,039,314). Such haloacetanilides may be illustrated by the general formula VII

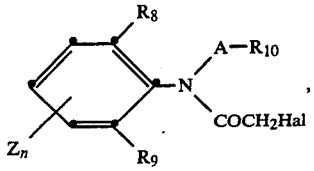

wherein Hal is halogen, preferably chlorine or bromine, each of $R_8$ and $R_9$ independently of the other is hydrogen, halogen, lower alkyl, alkoxy, alkylthio, haloalkyl, alkoxyalkyl or alkylthioalkyl, Z is hydrogen, halogen, lower alkyl, alkoxy, alkylthio, haloalkyl, alkoxylalkyl or alkylthioalkyl, which radicals Z are preferably in the 3-position with respect to the nitrogen atom, n is 0 to 3, A is alkylene, preferably methylene, 1,1-ethylene, and 1,2-ethylene which may be substituted by 1 or 2 lower alkyl groups, and $R_{10}$ is lower alkoxy, hydroxycarbonyl, alkoxycarbonyl, carbamoyl, N-alkylcarbamoyl, N,N-dialkylcarbamoyl, cyano, an unsubstituted or substituted nitrogen-containing heterocyclic radical, alkanoyl, unsubstituted or substituted benzoyl, unsubstituted or substituted 1,3,4-oxadiazol-2-yl, 1,3,4-thiadiazol-2-yl, 1,3,4-triazol-3-yl or 1,3,4-triazol-1-yl.

Typical examples of such haloacetanilides are:
N-ethoxymethyl-N-chloroacetyl-2-ethyl-6-methylaniline
N-chloroacetyl-N-methoxymethyl-2,6-diethylaniline
N-chloroacetyl-N-(2-methyoxyethyl)-2,6-dimethylaniline
N-(2-allyloxyethyl)-N-chloroacetyl-2,6-dimethylaniline
N-chloroacetyl-N-(2-n-propoxyethyl)-2,6-dimethylaniline
N-chloroacetyl-N-(2-isopropoxyethyl)-2,6-dimethylaniline
N-chloroacetyl-N-(2-methoxyethyl)-2-ethyl-6-methylaniline
N-chloroacetyl-N-(methoxyethyl)-2,6-diethylaniline
N-(2-ethoxyethyl)-N-chloroacetyl-2-ethyl-6-methylaniline
N-chloroacetyl-N-(2-methoxy-1-methylethyl)-2-methylaniline
N-chloroacetyl-N-(2-methoxy-1-methylethyl)-2,6-dimethylaniline
N-chloroacetyl-N-(2-methoxy-1-methylethyl)-2,6-diethylaniline
N-chloroacetyl-N-(2-methoxy-1-methylethyl)-2-ethyl-6-methylaniline
N-(2-ethoxyethyl)-N-chloroacetyl-2,6-diethylaniline
N-chloroacetyl-N-(2-n-propoxyethyl)-2-ethyl-6-methylaniline
N-chloroacetyl-N-(2-n-propoxyethyl)-2,6-diethylaniline
N-chloroacetyl-N-(2-isopropoxyethyl)-2-ethyl-6-methylaniline
N-ethoxycarbonylmethyl-N-chloroacetyl-2,6-dimethylaniline
N-ethoxycarbonylmethyl-N-chloroacetyl-2,6-diethylaniline
N-chloroacetyl-N-(2-methoxy-1-methylethyl)-2,6-diethylaniline
N-chloroacetyl-N-(2-methoxy-1-methylethyl)-2-ethyl-6-methylaniline
N-(2-ethoxyethyl)-N-chloroacetyl-2,6-diethylaniline
N-chloroacetyl-N-(2-n-propoxyethyl)-2-ethyl-6-methylaniline
N-chloroacetyl-N-(2-n-propoxyethyl)-2,6-diethylaniline
N-chloroacetyl-N-(2-isopropoxyethyl)-2-ethyl-6-methylaniline
N-ethoxycarbonylmethyl-N-chloroacetyl-2,6-dimethylaniline
N-ethoxycarbonylmethyl-N-chloroacetyl-2,6-diethylaniline
N-chloroacetyl-N-methoxycarbonylmethyl-2,6-dimethylaniline
N-chloroacetyl-N-(2,2-diethoxyethyl)-2,6-dimethylaniline
N-chloroacetyl-N-(2-methoxy-1-methylethyl)-2,3-dimethylaniline
N-(2-ethoxyethyl)-N-chloroacetyl-2-methylaniline
N-chloroacetyl-N-(2-methoxyethyl)-2-methylaniline
N-chloroacetyl-N-(2-methoxy-2-methylethyl)-2,6-dimethylaniline
N-(2-ethoxy-2-methylethyl)-N-chloroacetyl-2-ethyl-6-methylaniline
N-chloroacetyl-N-(1-ethyl-2-methoxyethyl)-2,6-dimethylaniline
N-chloroacetyl-N-(2-methoxyethyl)-2-methoxy-6-methylaniline
N-n-butoxymethyl-N-chloroacetyl-2-tert-butylaniline
N-(2-ethoxyethyl-1-methylethyl)-2,6-dimethylaniline
N-chloroacetyl-N-(2-methoxyethyl)-2-chloro-6-methylaniline
N-(2-ethoxyethyl)-N-chloroacetyl-2-chloro-6-methylaniline
N-(2-ethoxyethyl)-N-chloroacetyl-2,3,6-trimethylaniline
N-chloroacetyl-1-(2-methoxyethyl)-2,3,6-trimethylaniline
N-chloroacetyl-N-cyanomethyl-2,6-dimethylaniline
N-but-3-yn-1-yl-N-chloroacetylaniline
N-chloroacetyl-N-propargyl-2-ethyl-6-methylaniline
N-chloroacetyl-N-(1,3-dioxolan-2-ylmethyl)-2,6-dimethylaniline
N-chloroacetyl-N-(1,3-dioxolan-2-ylmethyl)-2-ethyl-6-methylaniline
N-chloroacetyl-N-(1,3-dioxan-2-ylmethyl)-2-ethyl-6-methylaniline
N-chloroacetyl-N-(1,3-dioxan-2-ylmethyl)-2-ethyl-6-methylaniline
N-chloroacetyl-N-(2-furanylmethyl)-2,6-dimethylaniline
N-chloroacetyl-N-(2-furanylmethyl)-2-ethyl-6-methylaniline
N-chloroacetyl-N-(2-tetrahydrofuranylmethyl)-2,6-dimethylaniline
N-chloroacetyl-N-(N-propargylcarbamoylmethyl)-2,6-dimethylaniline
N-chloroacetyl-N-(N,N-dimethylcarbamoylmethyl)-2,6-dimethylaniline
N-(n-butoxymethyl)-N-chloroacetyl-2,6-diethylaniline
N-(2-n-butoxyethyl)-N-chloroacetyl-2,6-diethylaniline
N-chloroacetyl-N-(2-methoxy-1,2-dimethylethyl)-2,6-dimethylaniline
N-chloroacetyl-N-isopropyl-2,3-dimethylaniline
N-chloroacetyl-N-isopropyl-2-chloroaniline
N-chloroacetyl-N-(1H-pyrazol-1-ylmethyl)-2,6-dimethylaniline
N-chloroacetyl-N-(1H-pyrazol-1-ylmethyl)-2-ethyl-6-methylaniline N-chloroacetyl-N-(1H-1,2,4-triazol-1-ylmethyl)-2,6-dimethylaniline
N-chloroacetyl-N-(2H-1,2,4-triazol-1-ylmethyl)-2,6-diethylaniline
N-benzoylmethyl-N-chloroacetyl-2,6-dimethylaniline
N-benzoylmethyl-N-chloroacetyl-2-ethyl-6-methylaniline
N-chloroacetyl-N-(5-methyl-1,3,4-oxiadiazol-2-yl)-2,6-diethylaniline
N-choloracetyl-N-(5-methyl-1,3,4-oxadiazol-2-yl)-2-ethyl-6-methylaniline
N-chloroacetyl-N-(5-methyl-1,3,4-oxadiazol-2-yl)-2-tert-butylaniline
N-chloroacetyl-N-(4-chlorobenzoylmethyl)-2,6-dimethylaniline
N-chloroacetyl-N-(1-methyl-5-methylthio-1,3,4-triazol-2-ylmethyl)-2,6-diethylaniline.

Further haloacetanilides whose harmful effects on cultivated plants can be antagonised by the novel oxime ethers of the formula I are listed in R. Wegler, Chemie der Pflanzenschutz- und Schädlingsbekämpfungsmittel, Vol. 8, pp. 90–93 and pp. 322–327.

Numerous herbicidal thiocarbamates whose phytotoxic action on cultivated plants can be antagonised by the novel oxime ethers of the formula I are also known (q.v. for example U.S. Pat. Nos. 2,913,327, 3,037,853, 3,175,897, 3,185,720, 3,198,786, 3,582,314 and 3,846,115). The protective action of the novel oxime ethers of the formula I can be utilised particularly when applying thiocarbamates in cereals, rice or sorghum.

The thiocarbamates against whose phytotoxic action cultivated plants such as cereals, rice and sorghum may particularly be protected, have the general formulae IX and X:

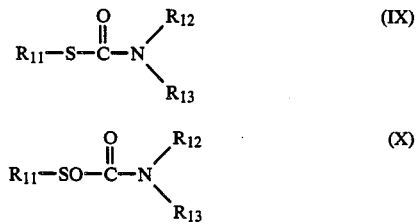

wherein $R_{11}$ is lower alkyl, alkenyl, chloroallyl, dichloroallyl, trichloroallyl, benzyl or 4-chlorobenzyl, $R_{12}$ is $C_2$–$C_4$ alkyl and $R_{13}$ is $C_2$–$C_4$ alkyl or cyclohexyl, and $R_{12}$ and $R_{13}$ together with the nitrogen atom to which they are attached can form a hexahydro1H-azepine, decahydroquinoline or 2-methyldecahydroquinoline ring.

Typical individual representatives of such thiocarbamates are:
S-ethyl-N,N-dipropylthiocarbamate
S-ethyl-N,N-diisobutylthiocarbamate
S-2,3-dichloroallyl-N,N-diisopropylthiocarbamate
S-propyl-N-butyl-N-ethylthiocarbamate
S-2,3,3-trichloroallyl-N,N-diisopropylthiocarbamate
S-propyl-N,N-dipropylthiocarbamate
S-ethyl-N-ethyl-N-cyclohexylthiocarbamate
S-ethyl-N-hexahydro-1H-azepine-1-carbothioate
S-isopropyl-N,N-hexamethylene-thiocarbamate
S-(p-chlorobenzyl)-N,N-diethylthiocarbamate
N-ethylthiocarbonyl-cis-decahydroquinoline
N-propylthiocarbonyl-decahydroquinalidine
S-ethyl-N,N-bis(n-butyl)-thiocarbamate
S-tert-butyl-N,N-bis(n-propyl)-thiocarbamate.

In addition to the chloroacetanilides and thiocarbamates, herbicides of other compound classes are also possible, e.g.:

Triazines and triazinones: 2,4-bis(isopropylamino)-6-methylthio-1,3,5-triazine ("prometryn"), 2,4-bis(ethylamino)-6-methylthio-1,3,5-triazine ("symetryn"), 2-(1',2'-dimethylpropylamino)-4-ethylamino-6-methylthio-1,3,5-triazine ("dimethametryn"), 4-amino-6-tert-butyl-4,5-dihydro-3-methylthio-1,2,4-triazin-5-one ("metribuzin").

Phenylureas: N-(3',4'-dimethylbenzyl)-N'-4-tolylurea (Dimuron ®), N-(3'-chloro-4'-isopropylphenyl)-N',N'-(3-methyl-pentamethylen-1,3-yl)urea.

Chloroacetamides: N-[1-isopropyl-2-methylpropen-1-yl(1)]-N-(2'-methoxyethyl)-chloroacetamide.

Diphenyl ethers and nitrodiphenyl ethers: 2,4-dichlorophenyl-4'-nitrophenyl ether ("nitrofen"), 2-chloro-1-(3'-ethoxy-4'-nitrophenoxy)-4-trifluoromethylbenzene ("oxyfluorfen"), 2',4'-dichlorophenyl-3-methoxy-4-nitrophenyl ether ("chlormethoxynyl"), methyl 2-[4'-(2'',4''-dichlorophenoxy)phenoxy]propionate, N-(2'-phenoxyethyl)-2-[5'-(2''-chloro-4''-trifluoromethylphenoxy)-phenoxy]propionamide.

Benzoic acid derivatives: methyl-5-(2',4'-dichlorophenoxy)-2-nitrobenzoate ("bifenox"), 5-(2'-chloro-4'-trifluoromethylphenoxy)-2-nitrobenzoic acid ("acifluorfen"), 2,6-dichlorobenzonitrile ("dichlobenil").

Nitroanilines: 2,6-dinitro-N,N-dipropyl-4-trifluoromethylaniline ("trifluralin"), N(1'-ethylpropyl)-2,6-dinitro-3,4-xylidine ("pendimethalin").

Oxadiazolones: 5-tert-butyl-3(2',4'-dichloro-5'-isopropoxyphenyl)-1,3,4-oxadiazol-2-one ("oxadiazon").

Phosphates: S-2-methylpiperidinocarbonylmethyl-0,0-dipropylphosphorodithioate ("piperophos").

Pyrazoles: 1,3-dimethyl-4-(2',4'-dichlorobenzoyl)-5-(4'-tolylsulfonyloxy)pyrazole.

Further herbicides are the derivatives of α-[4-(phenoxy)phenoxy]propionic acid or of α-[4-(pyridyl-2-oxy)phenoxy]propionic acid, which have the formula XI

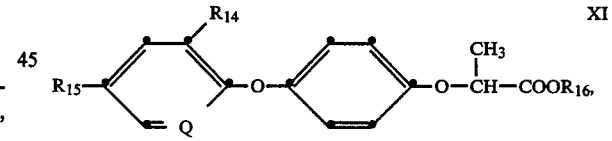

wherein
$R_{14}$ is hydrogen or halogen,
$R_{15}$ is hydrogen, halogen or trifluoromethyl,
Q is the fragment =N— or =CH—,
$R_{16}$ is $C_1$–$C_4$ alkyl, unsubstituted or substituted by $C_1$–$C_4$ alkoxy, or is $C_3$–$C_4$ alkenyl, $C_3$–$C_4$ alkynyl or

wherein $R_{17}$ is $C_1$–$C_4$ alkyl, $R_{18}$ is $C_1$–$C_4$ alkyl or $R_{17}$ and $R_{18}$ together are $C_1$–$C_5$ alkylene.

The amount of antidote employed varies from about 0.01 to about 15 parts by weight per part by weight of herbicide. The most suitable ratio in respect of optimum action on the particular cultivated plant is established from case to case, i.e. depending on the type of herbicide employed.

The oxime ethers of the formula I are also suitable for influencing plant growth. For example, they stimulate the root growth of seedlings, especially cereal, maize and rice seeds, so as to make possible the forced cultivation of such crops, e.g. under unfavourable climatic conditions or in intensive crop rotation.

The compounds of the formula I are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The formulations, i.e. the compositions containing the compound (active ingredient) of the formula I and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalates or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethylsulfoxide or dimethylformamide, as well as epoxidised vegetable oils such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of the formula I to be formulated, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids ($C_{10}$-$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts of unsubstituted or substituted ammoniums salts and contain a $C_8$-$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of poloxyethylene sorbitan and polyoxyethylene sorbitan trioleate are also suitable non-ionic surfactants.

Cationic surfactants are preferably quaternary ammonium salts which contain, as N-substituent, at least one $C_8$-$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloirde or benzyldi(2-chloroethyl)ethylammonium bromide.

The surfactants customarily employed in the art of formulation are described e.g. in "McCutcheon's Detergents and Emulsifiers Annual", MC Publishing Corp. Ringwood, N.J., 1979, and Sisely and Wood, "Encyclopedia of Surface Active Agents", Chemical Publishing Co., Ing. New. York, 1964.

These compositions usually contain 0.1 to 99%, preferably 0.1 to 95%, of a compound of the formula I, 1 to 99% of a solid or liquid adjuvant, and 0 to 25%, preferably 0.1 to 25%, or a surfactant.

Whereas commercial products are preferably formulated as concentrates, the end user will normally employ dilute formulations.

The compositions may also contain further ingredients, such as stabilisers, antifoams, viscotity regulators, binders, tackifiers as well as fertilisers or other active ingredients in order to obtain special effects.

The invention is illustrated in more detail by the following Examples, without implying any restriction to what is described therein. Parts and percentages are by weight.

EXAMPLE 1

Preparation of N-(1,3-dioxolan-5-yl-methoxy)imino-para-chloro-phenylacetonitrile (compound 4)

In a 100 ml round flask, 22.6 g (0.10 mole) of the sodium salt of 2-(4-chlorphenyl)-2-hydroximinoacetonitrile are dissolved in 50 ml of dimethylsulfoxide, Then 13.4 g (0.11 mole) of 5-chloromethyl-1,3-dioxolane are added dropwise to this solution and the mixture is stirred for 4 hours at 60° to 70° C. The resultant suspension is then cooled and poured into a mixture of ice/water. The reaction product is obtained from the mixture by extraction with methylene chloride. The extract is dried over sodium sulfate and the solvent is removed by evaporation. The crude reaction product is an orange oil which is distilled in a high vacuum at a bath temperature of 130° C., affording 15.8 g (59.2% of theory) of N-(1,3-dioxolan-5-yl-methoxy)imino-para-chlorphenylacetonitrile in the form of a colourless oil with a refractive index of $n_D^{20}$: 1.5690.

EXAMPLE 2

Preparation of N-(2-methyl-1,3-dioxolan-5-yl)methoxy)imino-para-chlorophenylacetonitrile (compound 5)

In a 100 ml round flask, 22.6 g (0.10 mole) of the sodium salt of 2-(4-chlorphenyl)-2-hydroximinoacetonitrile are dissolved in 50 ml of dimethylsulfoxide. Then 14.9 g (0.11 mole) of 5-chloromethyl-2-methyl-1,3-dioxolane are added dropwise to this solution and the mixture is stirred for 4 hours at 60°–70° C. The resultant suspension is then cooled and poured into a mixture of ice/water. The reaction product is obtained from the mixture by extraction with methylene chloride. The extract is dried over sodium sulfate and the solvent is removed by evaporation. The crude reaction product is an orange oil which is distilled in a high vacuum at a bath temperature of 130° C., affording 17 g (60.5% of theory) of N-(2-methyl-1,3-dioxolan-5-yl-methoxy)imino-para-chlorophenylacetonitrile in the form of a colourless oil with a refractive index of $n_D^{20}$: 1.5880.

The following compounds are prepared in similar manner:

| No. | X | Phenyl substitution (R$_2$ R$_3$ R$_4$) | $R_1$ (CH)$_n$ | CR$_5$R$_6$ | Physical data (°C.) |
|---|---|---|---|---|---|
| 1 | CF$_3$ | — | CH$_2$ | CH$_2$ | b.p. 82–84°/0.08 mbar |
| 2 | CF$_3$ | 4-Cl | CH$_2$ | CH$_2$ | $n_D^{20}$ 1.4985 |
| 3 | CN | — | CH$_2$ | CH$_2$ | $n_D^{20}$ 1.5500 |
| 4 | CN | 4-Cl | CH$_2$ | CH$_2$ | $n_D^{20}$ 1.5690 |
| 5 | CN | 4-Cl | CH$_2$ | CHCH$_3$ | $n_D^{20}$ 1.5580 |
| 6 | CN | — | CH$_2$ | CHCH$_3$ | $n_D^{20}$ 1.5370 |
| 7 | CN | — | CH$_2$ | CHC$_2$H$_5$ | $n_D^{20}$ 1.5330 |
| 8 | CN | — | CH$_2$ | C(CH$_3$)$_2$ | m.p. 62–63° |
| 9 | CN | — | CH$_2$ | CH(C$_3$H$_7$i) | $n_D^{20}$ 1.5280 |
| 10 | CN | 2-Cl | CH$_2$ | CH$_2$ | $n_D^{20}$ 1.5660 |
| 11 | CN | 3-Cl | CH$_2$ | CH$_2$ | $n_D^{20}$ 1.5650 |
| 12 | CN | 2-F | CH$_2$ | CH$_2$ | $n_D^{20}$ 1.5400 |
| 13 | CN | 2-F | CH$_2$ | CH(CH$_3$) | $n_D^{20}$ 1.5290 |
| 14 | CN | 4-F | CH$_2$ | CH$_2$ | $n_D^{20}$ 1.5530 |
| 15 | CN | 2,4Cl$_2$ | CH$_2$ | CH$_2$ | $n_D^{20}$ 1.5770 |
| 16 | CN | 4-Cl | CH$_2$ | CHC$_2$H$_5$ | $n_D^{20}$ 1.5500 |
| 17 | CN | 2-CH$_3$ | CH$_2$ | CH$_2$ | |
| 18 | CN | 3-CH$_3$ | CH$_2$ | CH$_2$ | $n_D^{20}$ 1.5490 |
| 19 | CN | 4-CH$_3$ | CH$_2$ | CH$_2$ | $n_D^{20}$ 1.5490 |
| 20 | CN | 2-OCH$_3$ | CH$_2$ | CH$_2$ | $n_D^{20}$ 1.5350 |
| 21 | CN | 3-OCH$_3$ | CH$_2$ | CH$_2$ | $n_D^{20}$ 1.5540 |
| 22 | CN | 4-CH$_3$O | CH$_2$ | CH$_2$ | $n_D^{20}$ 1.5670 |
| 23 | CN | 4-Br | CH$_2$ | CH$_2$ | $n_D^{20}$ 1.5820 |
| 24 | CN | 3,4 Cl$_2$ | CH$_2$ | CH$_2$ | wax-like |
| 25 | CN | 2,3-CH=CH—CH=CH— | CH$_2$ | CH$_2$ | oil |
| 26 | CF$_3$ | 2-Cl | CHCH$_3$ | C(CH$_3$)$_2$ | |
| 27 | CN | — | CHCH$_3$ | CH$_2$ | |
| 28 | CF$_3$ | — | — | C(CH$_3$)$_2$ | |
| 29 | CN | 3-Cl | — | CH$_2$ | |
| 30 | CN | 4-Cl | — | CHC$_2$H$_5$ | |
| 31 | CN | 4-Cl | — | C(C$_2$H$_5$)$_2$ | |
| 32 | CN | 4-CF$_3$ | — | CH$_2$ | |
| 33 | CF$_3$ | 4-Cl | — | C(CH$_3$)$_2$ | |
| 34 | CF$_3$ | 4-Cl | — | C(C$_2$H$_5$)$_2$ | |
| 35 | CF$_3$ | 4-Cl | — | C(CH$_3$)C$_2$H$_5$ | |
| 36 | CF$_3$ | 4-CH$_3$ | — | CH$_2$ | |

-continued

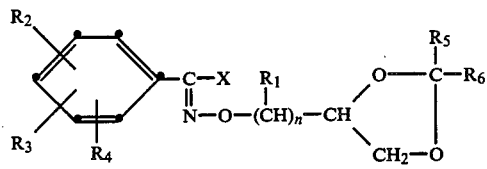

| No. | X | Phenyl substitution (R2 R3 R4) | $R_1$ \| (CH)n | CR5R6 | Physical data (°C.) |
|---|---|---|---|---|---|
| 37 | CF3 | 4-CH3 | — | C(CH3)2 | |
| 38 | CF3 | 4-CH3 | CH(CH3) | CH(CH3) | |
| 39 | CF3 | 4-CH3 | CH(CH3) | C)CH3)2 | |
| 40 | CN | 2-F | — | CH2 | |
| 41 | CN | 2-Cl | CH2 | CH(CH3 | |
| 42 | CN | 2-Cl | CH2 | CHC2H5 | |
| 43 | CN | 2-Cl | CH2 | C(CH3)2 | |
| 44 | CN | 2-Cl | CH2 | CHC3H7i | |
| 45 | CN | 3-Cl | CH2 | CHCH3 | |
| 46 | CN | 3-Cl | CH2 | CHC2H5 | |
| 47 | CN | 3-Cl | CH2 | C(CH3)2 | |
| 48 | CN | 3-Cl | CH2 | CHC3H7i | |
| 49 | CN | 4-Cl | CH2 | C(CH3)2 | |
| 50 | CN | 4-Cl | CH2 | CHC3H7i | |
| 51 | CN | 2-F | CH2 | CHC2H5 | |
| 52 | CN | 2-F | CH2 | C(CH3)2 | |
| 53 | CN | 2-F | CH2 | CHC3H7i | |
| 54 | CN | 4-F | CH2 | CHCH3 | |
| 55 | CN | 4-F | CH2 | CHC2H5 | |
| 56 | CN | 4-F | CH2 | C(CH3)2 | |
| 57 | CN | 4-F | CH2 | CHC3H7i | |
| 58 | CN | 2,4-Cl | CH2 | CHCH3 | |
| 59 | CN | 2,4-Cl2 | CH2 | CHC2H5 | |
| 60 | CN | 2,4 Cl2 | CH2 | C(CH3)2 | |
| 61 | CN | 2,4 Cl2 | CH2 | CHC3H7i | |
| 62 | CN | 2-CH3 | CH2 | CHCH3 | |
| 63 | CN | 2-CH3 | CH2 | CHC2H5 | |
| 64 | CN | 2-CH3 | CH2 | CHC3H7i | |
| 65 | CN | 2-CH3 | CH2 | C(CH3)2 | |
| 66 | CN | 4-Br | CH2 | CHCH3 | |
| 67 | CN | 4-Br | CH3 | C(CH3)2 | |
| 68 | CN | 4-Br | CH2 | CHC2H5 | |
| 69 | CN | 4-OCH3 | CH2 | C(CH3)2 | |
| 70 | CN | 4-OCH3 | CH2 | CHC2H5 | |
| 71 | CN | 3-OCH3 | CH2 | C(CH3)2 | |
| 72 | CN | 4-CH3 | CH2 | C(CH3)2 | |
| 73 | CF3 | — | CH2 | C(CH3)2 | |
| 74 | CF3 | — | CH2 | CH—C6H5 | |
| 75 | CF3 | 3,4 Cl2 | CH(CH3) | CHC6H4Cl(4) | |
| 76 | CF3 | 4-Cl | CH2 | CH2 | |
| 77 | CF3 | 4-Cl | CH2 | CHCH3 | |
| 78 | CN | 2CH34,6 Cl2 | CH2 | CHC2H5 | |
| 79 | CN | 2CH34,6Cl2 | CH(CH3) | CH2 | |
| 80 | CF3 | 2CH34,5Cl2 | CH2 | C(CH3)2 | |
| 81 | CN | — | CH2 | CHCF3 | |
| 82 | CN | 4-Cl | CH2 | CHCH2Cl | |
| 83 | CN | — | CH(CH)3CH(CH3) | CH2 | |
| 84 | CN | 4-Cl | CH(CH3)CH(CH3) | C(CH3)2 | |
| 85 | CF3 | 4-Cl | C2H4 | CH2 | |
| 86 | CN | 4-Cl | C2H4 | CH2 | |
| 87 | CN | — | CH2 | CH(CCl3) | |
| 88 | CN | 4-Cl | CH2 | CH(CCl3) | |
| 89 | CN | 4F | CH2 | CH(CCl3) | |
| 90 | CN | 4-CH3 | CH2 | CH—CH3 | $n_D^{24}$ 1.5400 |
| 91 | CN | 4-CH3 | CH2 | CH—C2H5 | $n_D^{24}$ 1.5370 |
| 92 | CN | 4-CH3 | CH2 | C(CH3)2 | $n_D^{24}$ 1.5340 |
| 93 | CN | 4-CH3 | CH2 | CH—CH(CH3)2 | $n_D^{24}$ 1.5315 |
| 94 | CN | 4-Cl | CH2 | C(CH3)2 | $n_D^{24}$ 1.5485 |
| 95 | CN | — | CH2 | cyclohexyl | |
| 96 | CN | — | CH2 | cyclopentyl | |

EXAMPLE 3

Formulation examples for compounds of formula I or mixtures thereof with herbicides (percentages are by weight

| (a) Wettable powders | (a) | (b) | (c) |
|---|---|---|---|
| Compound of formula I or mixture thereof with a herbicide | 20% | 60% | 0.5% |
| sodium lignosulfonate | 5% | 5% | 5% |
| sodium laurylsulfate | 3% | — | — |
| sodium diisobutylnaphthalene- | — | 6% | 6% |

| (a) Wettable powders | (a) | (b) | (c) |
|---|---|---|---|
| sulfonate | | | |
| octylphenol polyethylene glycol ether (7-8 moles of ethylene oxide | — | 2% | 2% |
| highly dispersed silicic acid | 5% | 27% | 27% |
| kaolin | 67% | — | — |
| sodium chloride | — | — | 59.5% |

The active ingredient is thoroughly mixed with the adjuvants and the mixture is thoroughly ground in a suitable mill, affording wettable powders which can be diluted with water to give suspensions of the desired concentration.

| (b) Emulsifiable concentrate | (a) | (b) |
|---|---|---|
| Compound of formula I or mixture thereof with a herbicide | 10% | 1% |
| octylphenol polyethylene glycol ether (4-5 moles of ethylene oxide) | 3% | 3% |
| calcium dodecylbenzenesulfonate castor oil polyglycolether (36 moles of ethyleneoxide) | 4% | 4% |
| cyclohexanone | 30% | 10% |
| xylene mixture | 50% | 79% |

Emulsions of any required concentration can be obtained from this concentrate by dilution with water.

| (c) Dusts | (a) | (b) |
|---|---|---|
| Compound of formula I or mixture thereof with a herbicide | 0.1% | 1% |
| talcum | 99.9% | — |
| kaolin | — | 99% |

Dusts which are ready for use are obtained by mixing the active ingredient with the carriers, and grinding the mixture in a suitable mill.

| (d) Extruder granulate | (a) | (b) |
|---|---|---|
| Compound of formula I or mixture thereof with a herbicide | 10% | 1% |
| sodium lignosulfonate | 2% | 2% |
| carboxymethylcellulose | 1% | 1% |
| kaolin | 87% | 96% |

The active ingredient is mixed and ground with the adjuvants, and the mixture is subsequently moistened with water. The mixture is extruded and then dried in a stream of air.

| (e) Coated granulate | |
|---|---|
| Compound of formula I or mixture thereof with a herbicide | 3% |
| polyethylene glycol 200 | 2% |
| kaolin | 94% |

The finely ground active ingredient is uniformly applied, in a mixer, to the kaolin moistened with polyethylene glycol. Non-dusty coated granulates are obtained in this manner.

| (f) Suspension concentrate | (a) | (b) |
|---|---|---|
| Compound of formula I or mixture thereof with a herbicide | 40% | 5% |
| ethylene glycol | 10% | 10% |
| nonylphenol polyethylene glycol ether | 6% | 1% |

| (f) Suspension concentrate | (a) | (b) |
|---|---|---|
| (15 moles of ethylene oxide) | | |
| sodium lignosulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the adjuvants, giving a suspension concentrate from which suspensions of any desired concentration can be obtained by dilution with water.

| (g) Salt solution | |
|---|---|
| Compound of formula I or mixture thereof with a herbicide | 5% |
| isopropylamine | 1% |
| octylphenol polyethylene glycol ether (78 moles of ethylene oxide) | 3% |
| water | 91% |

BIOLOGICAL EXAMPLES

The ability of the compounds of formula I to protect cultivated plants from the phytotoxic effects of potent herbicides is illustrated in the following Examples. In the test procedures the compounds of formula I are referred to as antidotes (safeners).

EXAMPLE 4

Preemergence test with antidote and herbicide in sorghum

Preemergence application of herbicide and antidote as tank mixture

Plastic containers measuring 25 cm × 12 cm are filled with sandy loam and Funk G 522 sorghum seeds are sown therein. The seeds are covered and a dilute solution of the safener for testing together with the herbicide is then sprayed as tank mixture onto the surface of the soil. The protective action of the safener is evaluated (in %) 30 days after application. The plants treated with herbicide alone and the completely untreated controls are used for reference purposes. The results are reported below.

Herbicide: 2-chloro-6'-ethyl-N-(2"-methoxy-1"-methylethyl)-acet-o-toluidide ("metolachlor").

Antidote: N-(4-methyl-1,3-dioxolan-5-yl-methoxy)imino-para-chlorophenylacetonitrile (compound 5).

| | Herbicide | Antidote compound 5 | Relative protective action (improvement in tolerance) |
|---|---|---|---|
| Rate of application in kg/ha | 1 | 1 | 50% |
| | 1 | 0.5 | 37.5% |

EXAMPLE 5

Test with antidote and herbicide in sorghum

Preemergence application of herbicide and antidote as tank mixture

Pots (diameter at the top 6 cm) are filled with sandy loam and Funk G 522 sorghum seeds are sown therein.

The seeds are covered and a dilute solution of the compound for testing as safener, together with the herbicide, is then sprayed as tank mixture onto the surface of the soil. The protective action of the safener is evaluated (in %) 21 days after application. The plants treated with herbicide alone and the completely untreated controls are used for reference purposes. The results are reported below.

Herbicide: 2-chloro-6'-ethyl-N-(2''-methoxy-1''-methylethyl)-acet-o-toluidide ("metolachlor")

| Rate of application Antidote | Herbicide | Relative protective action |
|---|---|---|
| No. 3 1.5 kg/ha | 1,5 kg/ha | 25% |
| No. 4 1.5 kg/ha | 1.5 kg/ha | 38% |
| No. 5 1.5 kg/ha | 1.5 kg/ha | 38% |
| No. 13 1.5 kg/ha | 1.5 kg/ha | 25% |
| No. 90 1.5 kg/ha | 1.5 kg/ha | 25% |
| No. 92 1.5 kg/ha | 1.5 kg/ha | 38% |

EXAMPLE 6

Test with antidote and herbicide in wheat

Postemergence application of herbicide and antidote as tank mixture

"Farnese" wheat seeds are sown in plastic pots (diameter at the top 11 cm) containing 0.5 liter of earth in a greenhouse. The seeds are covered and the compound for testing as safener is applied post-emergence, together with the herbicide, as tank mixture. The protective action of the safener is evaluated (in %) 20 days after application. The plants treated with herbicide alone and the completely untreated controls are used for reference purposes. The results are reported below:

Herbicide: Propynyl α-[4-(2',4'-dichloropyridyl-2'-oxo)-phenoxy]propionate.

| Rate of application Antidote | Herbicide | Relative protective action |
|---|---|---|
| No. 8 1.5 kg/ha | 0.75 kg/ha | 25% |
| No. 9 1.5 kg/ha | 0.75 kg/ha | 25% |
| No. 25 1.5 kg/ha | 0.75 kg/ha | 25% |

EXAMPLE 7

Test with antidote and herbicide in rice

Application of the antidote by immersion of the rice seeds, and preemergence application of the herbicide to the moist soil Rice seeds are immersed for 48 hours in 100 ppm solutions of the compound for testing as safener. The seeds are then allowed to dry for about 2 hours until they are no longer tacky. Plastic containers measuring 25 cm×17 cm×12 cm are filled with sandy loam to 22 cm below the edge. The pretreated seeds are sown on the surface of the soil in the containers and only lightly covered. The soil is kept in a moist (non-marshy) state. Then a dilute solution of the herbicide is sprayed onto the surface of the soil. The water level is then gradually raised in accordance with growth of the rice plants. The protective action of the safener is evaluated (in %) 18 days after application. The plants treated with herbicide alone and the completely untreated controls are used fo reference purposes. The results are as follows:

Herbicide: 2-chloro-2',6'-diethyl-N-(2''-propylethyl)acetanilide ("pretilachlor").

| Rate of application Antidote | Herbicide | Relative protective action |
|---|---|---|
| No. 11 100 ppm | 0.25 kg/ha | 25% |

EXAMPLE 8

Test with antidote and herbicide in soybeans

Preemergence application of herbicide and antidote as tank mixture

Pots (diameter at the top 6 cm) are filled with sandy loam and "Hark" soybean seeds are sown therein. The seeds are covered and a dilute solution of the compound for testing as safener, together with the herbicide, is sprayed as tank mixture onto the surface of the soil. The protective action is evaluated (in %) 21 days after application. The plants treated with herbicide alone and the completely untreated controls are used for reference purposes. The results are reported below.

Herbicide: 4-amino-6-tert-butyl-4,5-dihydro-3-methylthio-1,2,4-triazin-5(4H)-one ("metribuzin").

| Rate of application Antidote | Herbicide | Relative protective action |
|---|---|---|
| No. 25 1.5 kg/ha | 0.75 kg/ha | 25% |

EXAMPLE 9

Stimulation of the root growth of germinating wheat seeds

To determine the promotion of root growth, wheat seeds which have been dressed with 25 mg/kg of the compound for testing, as well as untreated wheat seeds of the same variety, are sown in a greenhouse in shallow plastic cylinders (5 cm×30 cm) filled with soil. Ten seeds are sown in each cylinder. The seedlings are carefully washed out of the soil 10 days later. The length and dry weight of the roots are determined and compared with the values obtained for the seedlings of untreated wheat. Compared with the controls, the growth in length and weight of the roots of seedlings treated with compounds 19, 90, 91 and 92 are respectively 17% and 21% greater.

What is claimed is:

1. A compound of the formula:

$$\underset{R_3}{\underset{\|}{\bigcirc}}-\underset{\|}{\overset{\phantom{|}}{C}}-X \quad \underset{N-O-(CH)_n-CH-CH_2}{\overset{R_1}{\underset{|}{\phantom{|}}} \quad \overset{R_5}{\underset{|}{\overset{\phantom{|}}{C}}}\overset{R_6}{\underset{|}{\phantom{|}}}}$$

wherein
R₁ is hydrogen or alkyl of 1 to 4 carbon atoms;
each of R₅ and R₆, independently of the other, is hydrogen, alkyl of 1 to 4 carbon atoms, or haloalkyl of 1 to 4 carbon atoms, or R₅ and R₆ together are alkylene or alkenylene of 2 to 6 carbon atoms;
X is cyano or trifluoromethyl; and
n is 1 or 2.

2. A compound of the formula:

$$\text{Cl}\underset{\underset{\text{N}-\text{O}-\text{CH}_2-\text{CH}-\text{CH}_2}{|}}{\overset{\text{C}-\text{CN}}{|}}\text{—}\underset{\text{O}\qquad\text{O}}{\overset{\overset{R_5\ R_6}{\diagdown\ \diagup}}{\underset{}{\text{C}}}}$$

wherein

R$_5$ and R$_6$ independently are hydrogen, methyl, or isopropyl.

3. A compound according to claim 1 wherein R$_3$ is chloro, R$_1$ is hydrogen, and R$_5$ and R$_6$ independently are hydrogen, methyl, or isopropyl.

4. A compound according to claim 1 wherein R$_3$ is chloro and X is cyano.

5. N-(1,3-Dioxolan-5-yl-methoxy)imino-para-chlorophenylacetonitrile according to claim 2.

6. N-(2-Methyl-1,3-dioxolan-5-yl-methoxy)imino-para-chlorophenylacetonitrile according to claim 2.

7. 1-(4-Chlorophenyl-1,3-dioxolan-5-yl-methoximino)-2,2,2-trifluoroethane according to claim 3.

8. N-(2,2-Dimethyl-1,3-dioxolan-5-yl-methoxy)imino-para-chlorophenylacetonitrile according to claim 2.

9. N-(2-Methyl-1,3-dioxolan-5-yl-methoxy)imino-ortho-fluorophenylacetonitrile according to claim 2.

10. A composition for the selective control of weeds in cultures of crop-plants, which contains as active component (a) a herbicidal haloacetanilide or a herbicidal thiocarbamate, and (b) a compound according to claim 2 as antidote, together with a suitable carrier.

11. A composition which contains as active component (a) a haloacetanilide herbicide of the formula $$\text{(benzene ring with } R_8, R_9, Z_n \text{ substituents)}-\underset{\text{COCH}_2\text{Hal}}{\overset{\text{A}-R_{10}}{\text{N}}}$$

wherein Hal is chlorine or bromine, each of R$_8$ and R$_9$ independently of the other is hydrogen, halogen, lower alkyl, alkoxy, alkylthio, haloalkyl, alkoxyalkyl or alkylthioalkyl, which radicals Z are preferably in the 3-position with respect to the nitrogen atom, n is 0 to 3, A is alkylene, preferably methylene, 1,1-ethylene, and 1,2-ethylene which may be substituted by 1 or 2 lower alkyl groups, and R$_{10}$ is lower alkoxy, hydroxycarbonyl, alkoxycarbonyl, carbamoyl, N-alkylcarbamoyl, N,N-dialkylcarbamoyl, cyano, an unsubstituted or substituted nitrogen-containing heterocyclic radical, alkanoyl, unsubstituted or substituted 1,3,4-oxadiazol-2-yl, 1,3,4-oxadiazol-2-yl, 1,3,4-thiadiazol-2-yl, 1,3,4-triazol-3-yl or 1,3,4-triazol-1-yl, and (b) a compound according to claim 2 as antidote, together with a suitable carrier.

12. A composition which contains
(a) a thiocarbamate of the formula $$R_{11}-S-\underset{\text{O}}{\overset{\|}{\text{C}}}-\text{N}\diagdown^{R_{12}}_{R_{13}} \quad \text{or} \quad R_{11}-\text{SO}-\underset{\text{O}}{\overset{\|}{\text{C}}}-\text{N}\diagdown^{R_{12}}_{R_{13}}$$

wherein R$_{11}$ is lower alkyl, alkenyl, chloroallyl, dichloroallyl, trichloroallyl, benzyl or 4-chlorobenzyl, R$_{12}$ is C$_2$–C$_4$ alkyl and R$_{13}$ is C$_2$–C$_4$ alkyl or cyclohexyl, and R$_{12}$ and R$_{13}$ together with the nitrogen atom to which they are attached can form a hexahydro-1H-azepine, decahydroquinoline or 2-methyldecahydroquinoline ring, and (b) a compound according to claim 2 as antidote, together with a suitable carrier.

13. A method of protecting cultivated plants from damage that may be caused by the application of herbicides, which method comprises (a) treating the locus of the plant before or during application of the herbicide, or (b) treating the seeds or seedlings of the plant itself with an effective amount of a compound according to claim 2.

* * * * *